US006854348B2

(12) United States Patent
Hoshida et al.

(10) Patent No.: US 6,854,348 B2
(45) Date of Patent: Feb. 15, 2005

(54) METHOD FOR COUNTING FOREIGN MATTER PARTICLES IN VINYL CHLORIDE-BASED RESIN POWDER AND APPARATUS SYSTEM THEREFOR

(75) Inventors: Shigehiro Hoshida, Ibaraki-ken (JP); Makoto Suzuki, Ibaraki-ken (JP); Hideo Yoshikoshi, Ibaraki-ken (JP); Osamu Matsumoto, Ibaraki-ken (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 394 days.

(21) Appl. No.: 10/213,953

(22) Filed: Aug. 8, 2002

(65) Prior Publication Data

US 2003/0041678 A1 Mar. 6, 2003

(30) Foreign Application Priority Data

Aug. 30, 2001 (JP) ...................................... 2001-262054
Sep. 19, 2001 (JP) ...................................... 2001-284773

(51) Int. Cl.[7] ............................................. G01N 15/02
(52) U.S. Cl. ....................................................... 73/866
(58) Field of Search ............................ 73/61.62, 61.66, 73/61.68, 61.69, 865.5, 866

(56) References Cited

U.S. PATENT DOCUMENTS 3,882,716 A * 5/1975 Beiman ...................... 73/61.66

FOREIGN PATENT DOCUMENTS

FR          2637983     * 4/1990   ................. 73/865.5

* cited by examiner

Primary Examiner—Robert Raevis
(74) Attorney, Agent, or Firm—Wenderoth, Lind & Ponack, L.L.P.

(57) ABSTRACT

The invention discloses a method for counting foreign matter particles in a vinyl chloride resin powder comprising the steps of: forming an aqueous dispersion of the resin particles in a vessel having a transparent bottom, allowing the particles to settle forming a layer together with the foreign matter particles and viewing the layer of the deposited particles through the transparent bottom of the vessel to count the foreign matter particles in the deposited layer. The invention also provides an apparatus system for automatically counting foreign matter particles which comprises a vessel having a transparent bottom, a feed means for the resin powder, a water supply means, a stirrer means to form an aqueous dispersion in the vessel, a viewing means such as a CCD camera for recording the bottom image of the deposited layer through the transparent bottom of the vessel, and a control means for bringing the various parts of the system into a sequential linkage motion.

15 Claims, 4 Drawing Sheets

METHOD FOR COUNTING FOREIGN MATTER PARTICLES IN VINYL CHLORIDE-BASED RESIN POWDER AND APPARATUS SYSTEM THEREFOR

BACKGROUND OF THE INVENTION

The present invention relates to a novel method for detecting and counting foreign matter particles contained in a powder of a vinyl chloride-based polymeric resin as well as to a simple and efficient automatic apparatus system used therefor. More particularly, the invention relates to a method and an apparatus system for detecting and counting foreign matter particles contained in a powder of a vinyl chloride-based resin for the purpose of controlling the process conditions and product quality in the production of the resin powder products as well as for inspection of the base resin materials in the molding process of the resin powders into shaped articles.

As is known, inspection of a powder product of a vinyl chloride-based polymeric resin, referred to simply as a VC resin hereinafter, for detecting and counting foreign matter particles therein is conducted heretofore by either of the following two methods. Namely, the first of the methods is a simple visual inspection method of the resin powder per se in which a suitable amount of the resin powder taken by sampling is mounted as such on a suitable sheet such as a paper sheet or plastic sheet and the number of foreign matter particles therein is counted by naked eyes or under a magnifying glass. As a modification of this first method, it is also undertaken that the powder sample is spread over a sheet in a uniform thin layer by using a vibrator such as those sold under the tradename of Synton Vibrator before visual counting of the particles. The second of the conventional inspection methods is also a visual counting method but counting is conducted not for the resin powder as such but conducted for a light-transmitting shaped article prepared by molding the resin powder in advance in the form of a film, tape or plate.

The above mentioned first method totally relies on a man power labor so that reliability or reproducibility of the results cannot be ensured without extremely delicate and careful setting of the conditions of inspection procedure. Accordingly, the time required for inspection of one sample of the resin products cannot be short enough as desired in spite of the seeming simplicity of the method. The use of a vibrator is also not so effective to ensure high uniformity of the powder layer as spread thereby to be not recommendable when reproducibility of the results is essential. Alternatively, the sample resin powder is dropped in small portions onto a vibrating trough of a vibrator to run down on the trough in a powder stream of which the number of foreign matter particles is visually counted. This method is also not very efficient due to requirement for skillfulness of the inspection workers.

In the second method, it is of course that inspection of the molded article must be preceded by a molding process of the resin powder under inspection taking a considerable length of time so that this method is not applicable to the in-process control of the VC resin production process even by setting aside the problem of costs required for resin molding. In addition, this method is unavoidably not free from the troubles due to eventual entering of extraneous foreign matter particles from ambience leading to an incorrectly biased result of the inspection so that this method is questionable as an inspection method of VC resin powder products per se. At any rate, these prior art methods each heavily rely on the ability of the inspection workers including their eyesight power so that the reliability or reproducibility of the results of inspection inherently cannot be very high.

With an object to overcome the defects in the above described man-power methods for counting the number of foreign matter particles in a VC resin powder, Japanese Patent Kokai 2-49147 proposes an automatic inspection machine for counting foreign matter particles in a VC resin powder comprising a means for removal of static electricity from the white sample powder, a hopper to receive the sample powder, a continuous vibration feeder means of the sample powder provided below the hopper, a transfer means for the sample powder provided below the discharging end of the feeder means, a gas laser scanning detector of the reflection type provided above the transfer means and a processing and indicating means of the data obtained in the detector, in which the sample powder after removal of static electricity is mounted continuously under vibration onto the transfer means to form a flat powder layer of a uniform thickness and then the foreign matter particles in the powder layer are detected and counted by means of the gas laser scanning detector.

In the inspection method by using this machine, it is necessary in order to form a flat powder layer of a uniform thickness that the VC resin powder after removal of static electricity is moistened with steam, water, surface active agent or alcoholic solvent so that the resin particles is kept in a freely dispersible condition without leaving any undispersed lumps. This requirement for dispersibility of the sample powder can of course be fulfilled only by taking a considerable length of time for the moistening works. In addition, it is a rather difficult matter to obtain a thin powder layer of a uniform thickness of 0.7 to 1.5 mm even after removal of static electricity from the VC resin powder. Accordingly, this method is also not quite efficient when a large number of VC resin powder samples are to be subjected to inspection of foreign matter particles as a daily routine work.

The importance of the above described inspection methods for counting foreign matter particles in a VC resin product is increasing in recent years to be in compliance with the progress of the VC resin producing process which is under a trend of switching from the traditional batch-wise process of suspension polymerization of vinyl chloride monomer to a continuous polymerization process through a closed polymerization reactor which is not opened over a quite long time for continuous running of polymerization. Needless to say, such a long-term continuous running of the polymerization process without intermission can be accomplished only by overcoming the most difficult problem due to deposition of resin scale on the inner surface of the reactor walls. While the traditional and most effective method for prevention of scale deposition is to coat the reactor walls with a scale deposition inhibiting agent and long-life scale deposition inhibiting agents have been developed for use in a continuous polymerization reactor, it is unavoidable, however, that the effectiveness of the scale deposition inhibiting coating layer is subject to a gradual decrease in the long run resulting in a gradually increasing amount of deposited resin scale on the reactor walls, which eventually falls off the reactor walls to enter the VC resin product as foreign matter particles in addition to the scale debris and other metallic and inorganic dust particles left on the reactor walls due to incomplete cleaning of the reactor periodically undertaken by opening the reactor.

It is eagerly desired therefore in the industry producing or using VC resin products to develop a convenient and efficient method and an apparatus system for detecting and counting foreign matter particles contained in a VC resin powder capable of giving reliable and reproducible results without taking a long time per one powder sample under inspection.

SUMMARY OF THE INVENTION

The present invention accordingly has an object, in view of the above described problems and disadvantages in the prior art methods and apparatuses, to provide a novel and improved method for detecting and counting foreign matter particles contained in a powder of a vinyl chloride-based polymeric resin to give reliable and reproducible results as well as to provide an automatic apparatus system used in practicing the method.

Thus, the method of the present invention for detecting and counting foreign matter particles contained in a powder of a vinyl chloride-based polymeric resin comprises the steps of:

(a) forming or introducing an aqueous dispersion of a powder of the vinyl chloride-based polymeric resin containing foreign matter particles in or into an agitation vessel having a flat bottom of which at least a part is made from a transparent material;

(b) allowing the aqueous dispersion standing still in the agitation vessel to effect settling of the resin particles and the foreign matter particles forming a layer of the deposited particles on the bottom of the vessel; and (c) counting the number of the foreign matter particles deposited on the bottom of the vessel from below through the transparent bottom of the vessel.

In particular, the amount of water in the aqueous dispersion of the VC resin powder is preferably in the range from 1 to 10000 parts by weight per part by weight of the resin powder. Though optional, it is advantageous that the aqueous medium for dispersion of the resin particles is admixed with a powder dispersion aid such as a surface active agent in order to accomplish more complete dispersion of the resin particles in the aqueous medium.

The automatic apparatus system of the invention for detecting and counting foreign matter particles contained in a powder of a vinyl chloride-based polymeric resin to practice the above described inventive method comprises, as an assembly:

(A) an agitation vessel having a flat bottom made from a transparent material;

(B) a powder-feed means capable of introducing a specified amount of the resin powder into the agitation vessel (A);

(C) a water-supply means capable of introducing a specified volume of water into the agitation vessel (A);

(D) a stirrer means capable of forming a uniform aqueous dispersion of particles of the resin powder by agitating water and the resin powder introduced into the agitation vessel (A); and (E) a photographic means capable of recording an image of the lower surface of the layer of the resin powder deposited on the bottom of the agitation vessel (A) through the transparent bottom.

It is preferable in the above described apparatus system that the above-mentioned various parts of the apparatus system are brought into a sequential linkage motion by means of (F) a control circuit unit.

DETAILED DESCRIPTION OF THE PREFERRED EMBODIMENTS

As is described above, the principle of the inventive method for counting foreign matter particles in a VC resin powder to be described below in more detail, in which the term of "parts" relative to the amount of a material always refers to "parts by weight", is relatively simple by comprising only the steps (a) to (c). In step (a) of the inventive method, an aqueous dispersion of the VC resin powder under inspection is introduced into or formed in situ in an agitation vessel having a flat bottom with transparency. Since the minimum requirement for the material of the agitation vessel is that the bottom of the vessel is made from a transparent material, any of the vessels such as glass beakers and transparent plastic beakers can be used as the agitation vessel. It is of course optional that other parts of the vessel than the bottom are made from an opaque or non-light-transmitting material including metallic materials such as copper, iron, aluminum and stainless steels, opaque plastic resins, paper boards and natural materials such as wooden materials. Excepting for the requirement that the vessel has a flat bottom, the configuration and volume capacity of the agitation vessel are not particularly limitative and can be selected depending on the particular cases.

The objective material to which the method of the present invention is applied is a powder of a vinyl chloride-based polymeric resin including homopolymers of vinyl chloride and copolymers of vinyl chloride as the principal comonomer with one or more of other comonomers copolymerizable with vinyl chloride, of which, in particular, the weight fraction of the vinyl chloride units is at least 50%, as well as chlorinated resin products of the homo- and copolymers. The method of the invention is also applicable to any VC resin-based composite materials in a powdery form such as the so-called VC resin compounds as a composite material prepared by compounding a VC resin with plasticizers, stabilizers and other additives.

Examples of the above mentioned comonomers copolymerizable with vinyl chloride include vinyl ester compounds such as vinyl acetate and vinyl propionate, alkyl esters of acrylic and methacrylic acids such as methyl (meth)acrylate and ethyl (meth)acrylate, α-olefins such as ethylene and propylene, alkyl vinyl ethers, acrylic acid, methacrylic acid, acrylonitrile, styrene and vinylidene chloride. These comonomers can be copolymerized with vinyl chloride either singly or as a combination of two kinds or more to give ternary or higher copolymers. The type of the polymerization process for the preparation of the VC resin powder to be subjected to inspection by the inventive method is not particularly limitative including suspension polymerization, microsuspension polymerization and emulsion polymerization provided that the polymerized resin is in the form of a fine powder.

The water used as the aqueous medium for the preparation of an aqueous dispersion of the VC resin particles, referred to as the dispersion water hereinafter, is not particularly limitative relative to the quality of water provided that the water is completely freed from any particulate foreign matters by filtration through a filter. Accordingly, the base water to be subjected to filtration is not limited to deionized water or city water but can be the water supplied in average chemical plants obtained from river water or underground water by simple filtration. It is preferable that the dispersion water is admixed beforehand with a dispersion aid such as surface active agents.

The aqueous dispersion of the VC resin particles in the dispersion water as the dispersion medium is prepared by vigorously agitating 1 part of the VC resin powder in 1 to 10000 parts of the dispersion water. When the amount of the dispersion water is too small, complete dispersion of the resin particles in the dispersion water can hardly be accomplished while no particular additional improvements can be obtained by excessively increasing the amount of the dispersion water rather with some disadvantages caused in handling of a so large volume of the aqueous dispersion.

The above mentioned surface active agent added to the aqueous dispersion of the VC resin particles or the dispersion water therefor as a dispersion aid is also not particularly imitative and any of those sold as a conventional fabric cleaning detergent can be used here including anionic surface active agents and non-ionic surface active agents. Besides these surface active agents, certain water-soluble polymeric materials can be used as the dispersion aid of the VC resin particles including partially saponified polyvinyl alcohols, polyethylene oxides, gelatins, vinyl acetate/maleic anhydride copolymeric resins and starches.

Examples of the above mentioned anionic surface active agent include salts of alkylsulfates, salts of polyoxyethylene alkyl ether sulfates, salts of polyoxyalkylene alkylphenyl ether sulfates, salts of N-acyl tauric acids, salts of alkylbenzene sulfonic acids, salts of polyoxyethylene alkylphenyl ether sulfonic acids, salts of α-olefinsulfonic acids, salts of alkylnaphthalene sulfonic acids, salts of alkyldiphenyl ether disulfonic acids, salts of alkylsulfosuccinic acids, salts of monoalkylsulfosuccinic acids, salts of polyoxyethylene alkyl ether sulfosuccinic acids, salts of fatty acids, polyoxyethylene alkyl ether acetates, salts of N-acylamino acids, salts of alkenylsuccinic acids, salts of alkylphosphates and salts of polyoxyethylene alkyl ether phosphates as well as free acid compounds corresponding to these salts.

Examples of the above mentioned non-ionic surface active agent include sorbitan fatty acid esters, glycerin fatty acid esters, polyglycerin fatty acid esters, propyleneglycol fatty acid esters, polyethyleneglycol fatty acid esters, sucrose fatty acid esters, polyoxyethylene alkyl ethers, polyoxypropylene alkyl ethers, polyoxyethylene alkylphenyl ethers, polyoxyethylene fatty acid esters, polyoxyethylene sorbitan fatty acid esters, polyoxyethylene sorbitol fatty acid esters, polyoxyethylene glycerin fatty acid esters, polyoxyethylene propyleneglycol fatty acid esters, polyoxyethylene castor oils, polyoxyethylene hardened castor oils, polyoxyethylene phytostanol ethers, polyoxyethylene phytosterol ethers, polyoxyethylene cholestanol ethers, polyoxyethylene cholesteryl ethers, polyoxyalkylene-modified organopolysiloxanes, polyoxyalkylene/alkyl co-modified organopolysiloxanes, polyoxyalkylene/fluoroalkyl co-modified organopolysiloxanes, polyoxyalkylene/ organopolysiloxane block copolymers, alkanolamides, sugar ethers and sugar amides.

The amount of the surface active agent added to the aqueous dispersion of the VC resin powder or dispersion water therefor is preferably in the range from 0.0000001 to 0.1 part per part of water, when added. Although addition of a surface active agent is optional and counting of foreign matter particles can be conducted even without using any surface active agent, addition of a surface active agent to the aqueous dispersion gives an advantage of saving the time taken for obtaining full dispersion of the resin particles in the aqueous medium. No particular additional improvements can be obtained, however, by increasing the amount thereof to exceed the above mentioned upper limit.

Dispersion of the VC resin particles in the aqueous dispersion medium is accomplished either by agitating the resin powder and dispersion water in a vessel with a stirrer rotating at an appropriate revolution velocity or by mechanically or manually shaking or tumbling the vessel containing the resin powder and dispersion water. Completeness of powder dispersion in the aqueous medium is one of the key factors for the inventive method to be successful giving reliable and reproducible results of counting of the foreign matter particles in the VC resin powder.

In step (b) of the inventive method, the agitation vessel containing the aqueous dispersion of the VC resin particles is kept standing still for a while so that settling of the resin particles proceeds in the aqueous dispersion resulting in deposition of the resin particles to form a thin deposit layer of the particles on the transparent bottom of the vessel together with the foreign matter particles. Since VC resin particles in general have a density larger than that of water, settling of the particles proceeds at a good velocity to be near to completion within 10 seconds or longer. It is preferable, however, to keep the vessel standing still for 0.5 to 15 minutes in order to ensure completeness of settling of particles.

The number of foreign matter particles contained in the VC resin powder and now deposited onto the bottom of the vessel in a thin layer of the resin powder as settled can be counted through the transparent part of the bottom by a variety of methods including direct counting of the particles with naked eyes, counting of the particles on a photographic picture of the vessel bottom taken with a camera and electronic data processing of an image of the vessel bottom recorded with a CCD camera.

In the following, the apparatus or apparatus system used for practicing the above described inventive method is illustrated in detail by making reference to the accompanying drawing.

As is summarized before, the apparatus system of the invention for detecting and counting foreign matter particles contained in a VC resin powder comprises, as an assembly:

(A) an agitation vessel having a flat bottom made from a transparent material;
(B) a powder-feed means capable of introducing a specified amount of the VC resin powder into the agitation vessel (A);
(C) a water-supply means capable of introducing a specified volume of water to the agitation vessel (A);
(D) a stirrer means capable of forming a uniform aqueous dispersion of the VC resin particles by agitating the water and the resin powder introduced into the agitation vessel (A);
(E) a photographic camera capable of recording the image of a layer of the resin powder deposited on the bottom of the agitation vessel (A) through the transparent bottom; and, optionally,
(F) a control circuit unit capable of bringing the above described component parts (A) to (E) into a sequential linkage motion.

In an example of the apparatus system of the present invention illustrated in FIG. 1 by a schematic overview, the VC resin powder P held in a hopper 6 of the automatic powder feeding unit (referred to as the feeder 2 hereinafter) is introduced into the agitation vessel 13 through a conduit 9 opening above the vessel 13 under vibration by actuating the vibrator 8. The feeder 2 comprises a turntable 5, which is supported by a vertical shaft 4 standing upright on a base table 1 and rotatable therearound by means of an electric motor 3. The turntable 5 supports a plurality of hoppers (for example, eight hoppers in this case) 6, each of which is provided with a damper 7 and a vibrator 8 to ensure exact feeding of the resin powder P into the vessel 13. FIG. 2 is a schematic plan view of the turntable 5 which is turnable around the vertical shaft 4 and supports eight hoppers 6,6 at a uniform distance each from the adjacent ones.

When one of the hoppers 6,6 is brought to a correct position suitable for feeding of the resin powder P into the agitation vessel 13 by the revolution of the turntable 5 around the shaft 4, the position of the hopper 6 can be detected by means of a photoelectric sensor 6A. Namely, rotation of the electric motor 3 is interrupted when the sensor 6A detects arrival of the hopper 6 at its correct angular position as brought by the rotating turntable 5.

Figure 1:
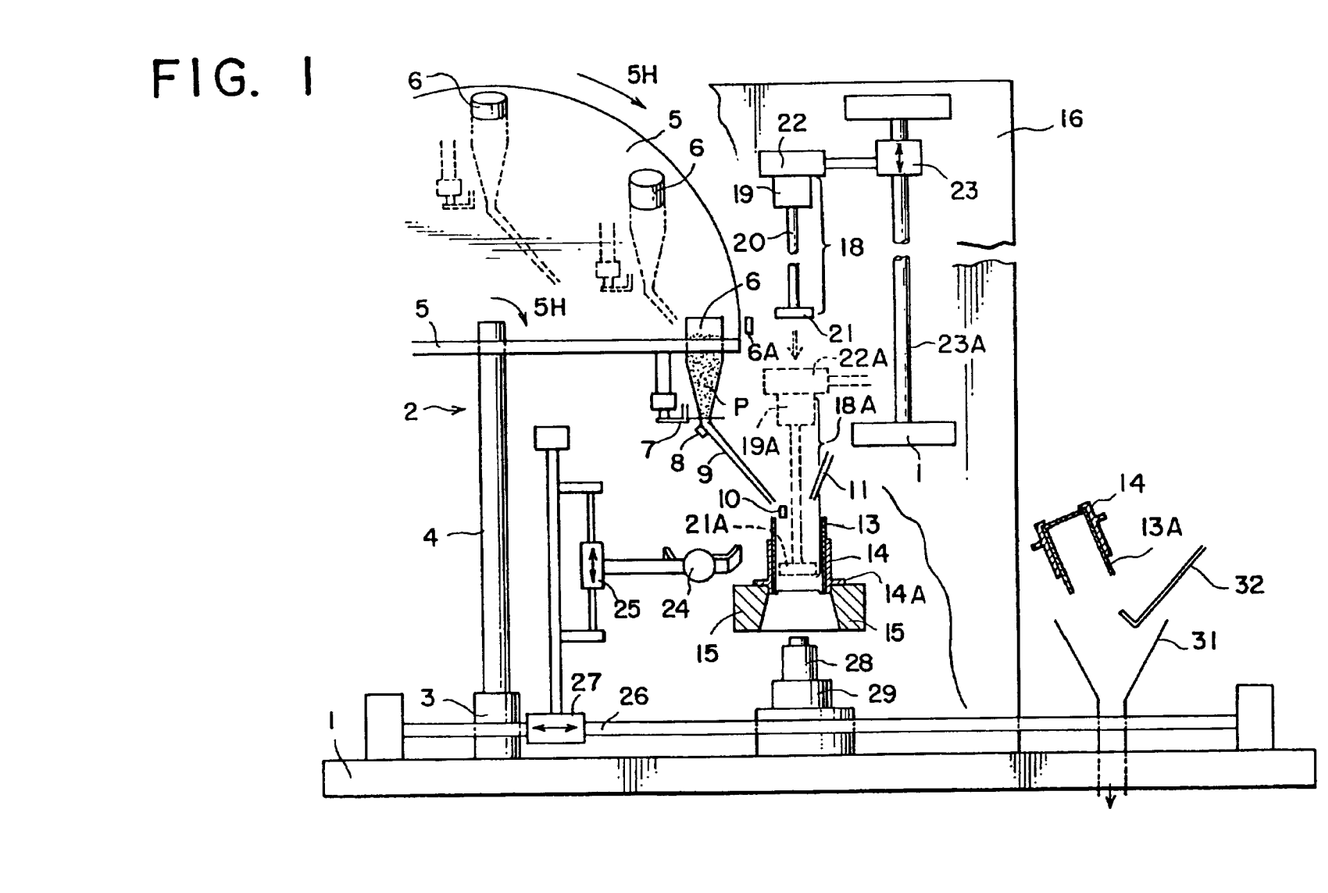
FIG. 1 is a schematic illustration of the front view of the inventive automatic apparatus system given as an example.
Figure 2:
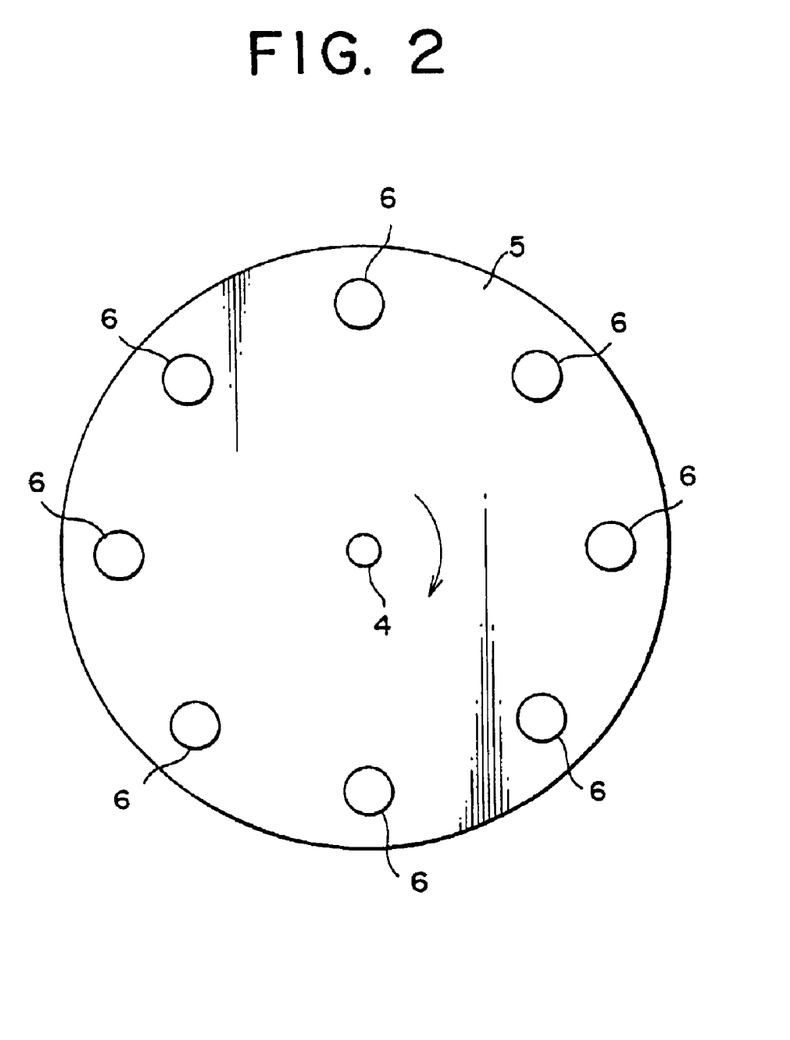
FIG. 2 is a schematic illustration of the arrangement of a plurality of hoppers on a turntable as a part of the resin powder-feed means in the inventive apparatus system.

Although FIGS. 1 and 2 each illustrate an automatic feeder means 2 as an example, which consists of a turntable 5 and a plurality of hoppers 6,6 supported thereon, the feeder means is not limited to this type provided that a weighed amount of the VC resin powder can be introduced portionwise into the agitation vessel 13. Suitable powder feeder means include pneumatic powder transfer means by using a blower or cyclone, screw conveyors, rotary disk dispensers connected to a belt conveyor, transfer feeders by a movable table, robotized-arm powder transfer feeders and so on. If necessary, two or more feeder means of different types can be used in combination.

Completion of introduction of a specified amount of the resin powder P into the agitation vessel 13 as falling out of the lower open end of the feeder conduit 9 connected to the bottom of the hopper 6 can be detected by a powder sensor 10 which detects reflection of a light beam directed therefrom to just below the conduit 9 and reflected by the falling resin powder P.

As is illustrated in FIG. 1, a water supply tube 11 connected to a water supply source 12 (not shown in the figure) is provided to open above the agitation vessel 13 and a specified volume of water is introduced therefrom into the vessel 13. It is advantageous in order to rapidly accomplish dispersion of the resin particles P coming from the hopper 6 and the dispersion water coming from the water supply tube 11 that the dispersion water from the tube 11 is admixed in advance with a surface active agent or the dispersion water is introduced into the vessel 13 concurrently with a surface active agent capable of being readily dissolved in water.

A further description is given, by making reference to FIG. 1, of the stirrer means by which the VC resin powder P and the dispersion water introduced into the agitation vessel 13 are agitated together to form a uniform aqueous dispersion. The stirrer means 18 (at the pulled-up standby position) or 18A (at the lowered working position) supported as a whole on the supporting board 16 and consisting of a stirrer shaft 20 (20A), stirrer blade 21 (21A) and electric motor 19 (19A) to drive the shaft 20 is supported by a supporting member 22 (22A) connected to an elevator 23 which can move up and down by sliding on the elevator stem 23A standing upright on the base table 1. The stirrer means, when in service to disperse the VC resin powder into the dispersion water, is at the lowered position indicated by 18A so that the stirrer blade 21A works to agitate the aqueous dispersion in the agitation vessel 13 while, when preparation of the aqueous dispersion has come to completion, the stirrer means is pulled up by the elevator 23.

The stirrer means 18 is a mechanism which serves to vigorously agitate the VC resin powder P and the dispersion water introduced into the agitation vessel 13 to form a uniform aqueous dispersion of the powder P in an aqueous medium. When formation of the aqueous dispersion has been completed in the agitation vessel 13, the stirrer means 18 is hoisted upwardly to the pulled-up standby position and the aqueous dispersion in the vessel 13 is kept standing still for a while to allow spontaneous settling of the VC resin particles in the aqueous dispersion forming a uniform thin layer of the VC resin particles on the flat bottom of the agitation vessel 13 secured in a bottom-less protecting receptacle 14 with a flange 14A standing on an annular base 15. Since the bottom of the agitation vessel 13 is made of a plate of a transparent material such as a glass plate or a plastic resin plate having transparency, the bottom image of the powder layer deposited on the bottom of the vessel 13 can be recorded by a camera 28 on a movable stand 29 through the transparent bottom of the vessel 13 together with foreign matter particles appearing here and there among the VC resin particles forming a uniform layer.

When the layer of the VC resin particles deposited on the bottom of the vessel 13 is poorly uniform eventually to leave fissures or other defects in the layer, it is possibly the case that the number of foreign matter particles as counted on the analysis of the photographic image record of the powder layer involves a positive error due to such defects hardly discriminatable from true foreign matter particles giving an excessively large number over the true number of the foreign matter particles. When the thickness of the deposited resin powder layer is too large, the result of counting of the foreign matter particles in the VC resin powder may involve a negative error because some of the foreign matter particles embedded in the resin powder layer fail to be detected from the bottom image of the deposited powder layer. When the thickness of the deposited powder layer is too small, on the other hand, the interstices between resin particles are sometimes erroneously counted as foreign matter particles to cause a positive error. In this regard, it is preferable that the deposited resin powder layer has a uniform thickness in the range from 0.1 to 6.0 cm.

The type of the stirrer blade 21 connected to the stirrer shaft 20 is not particularly limitative but a propeller blade or paddle blade is preferable for direct dispersion although a uniform dispersion can be obtained by an indirect method in which the agitation vessel 13 containing the resin powder and dispersion water is shaken as a whole or vibration is caused by applying ultrasonic waves.

The agitation vessel 13, in which a uniform aqueous dispersion of the VC resin powder is prepared, should have a flat bottom made from a transparent material. For example, a cylindrical glass-made vessel can be used for the purpose if the vessel has a flat bottom. The form of the agitation vessel 13 is not limited to a cylindrical one but can be of the form of a frustum of a cone. The transparent material forming the bottom of the agitation vessel 13 can be, besides various kinds of glass materials, a plastic resin having transparency such as acrylic resins and polycarbonate resins. It is not always necessary that the agitation vessel 13 is monolithically formed from a single transparent material but can be an assembly formed from a tubular body of a stainless steel and a disk or circular plate of a transparent material conjoined to one end of the tubular body as a flat bottom.

It is advantageous that a plurality of agitation vessels 13 are ready for use and the preparatory procedure including evacuation of one of the vessels by discharging the aqueous dispersion after inspection and cleaning of the vessel for the next run of inspection can be carried out concurrently with the inspection procedure of the next run including preparation of an aqueous dispersion of the VC resin powder in another vessel followed by settling of the resin particles and counting of the foreign matter particles.

The preparatory procedure down to setting of the agitation vessel 13 as secured in a protecting receptacle 14 with a flange 14A on an annular base 15 can be undertaken by means of an automatic robot machine which consists of a base runner 27 capable of moving back and forth along a horizontal guide rail 26, an elevator 25 movable up and down along a vertical stem and a robotized grip 24 held at the end of a cantilever arm connected to the elevator 25.

Figure 3:
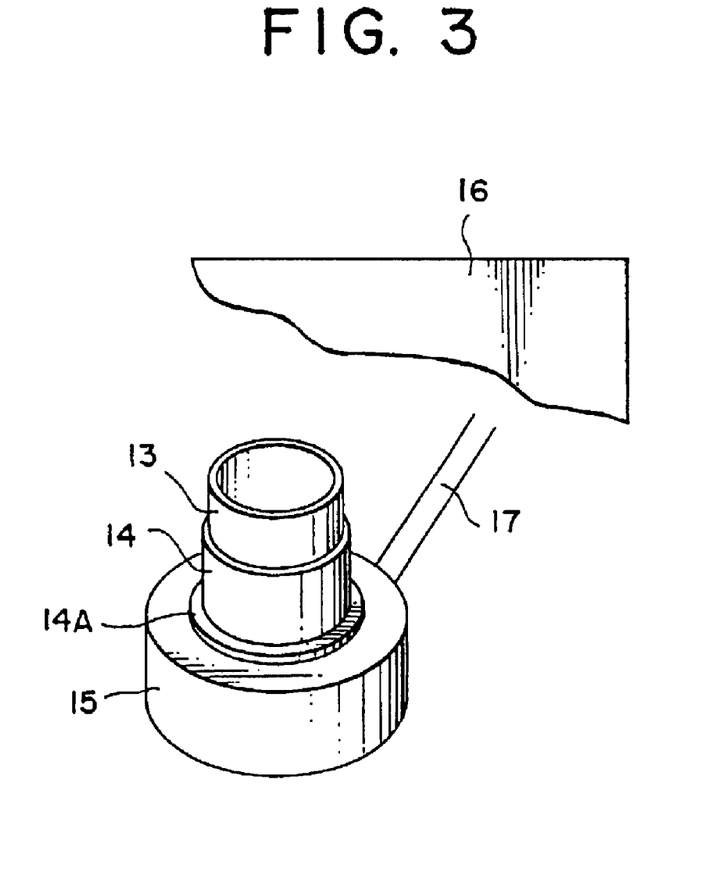
FIG. 3 is a schematic perspective view showing the agitation vessel kept standing on an annular base.

When an inspection run to count the foreign matter particles in a sample of the VC resin powder has been completed in an agitation vessel 13 with the stirrer means 18 brought to the pulled-up standby position, the robot grip 24 reaches the vessel 13 by operating the horizontal runner 27 and the elevator 25 and the vessel 13 containing the aqueous dispersion after completion of the inspection procedure as held in a flanged protecting receptacle 14 is grasped by the robot grip 24 and taken up from the annular base 15 connected to the supporting board 16 by a supporting arm 17 (see FIG. 3) to be brought by the movement of the runner 27 just above the drain funnel 31 where the vessel 13 is turned over into an upside-down disposition 13A for evacuation of the aqueous dispersion and then cleaned with washing water ejected out of the water nozzle 32 to be ready for the next inspection run for another sample of VC resin powders.

In conducting an inspection run of a VC resin powder sample for the number of foreign matter particles contained therein, the agitation vessel 13 cleaned in the above described manner and held in the protecting receptacle 14 is grasped by the robot grip 24 and set up again on the annular base 15 which is supported by a supporting arm 17 fixed to the supporting backboard 16 (see FIG. 3) by operating the elevator 25 and the horizontal runner 27. As the agitation vessel 13 is set on a correct position for measurement as shown in FIG. 1, a specified amount of the VC resin powder sample P for inspection is introduced thereinto via the powder feed conduit 9 coming from one of the resin powder hoppers 6 on a turntable 5 revolvable around the shaft 4, of which the angle of revolution is controlled by means of the position sensor 6A, under monitoring by the sensor 10. On the other hand, a specified volume of the dispersion water coming from a water supply source (not shown in the figure) is introduced into the agitation vessel 13 through the water supply tube 11. Thereafter, the agitation means 18 is lowered to the lowered working position 18A and agitation of the resin particles P in the dispersion water is started by turning the electric motor 19 on into operation. As a uniform aqueous dispersion of the VC resin powder is obtained in the agitation vessel 13, the stirrer means 18A is stopped and brought up to the pulled-up standby position 18 and the aqueous dispersion is kept standing still for a while so as to allow the resin particles deposited on the transparent bottom of the vessel 13 carrying the foreign matter particles contained in the resin powder to form a thin layer of the deposited particles on the bottom of the vessel 13 so that the number of the foreign matter particles can be counted by viewing from below through the transparent bottom of the vessel 13.

The process of counting the foreign matter particles appearing on the bottom surface of the deposited layer of VC resin particles is conducted with a camera 28 focusing the lens to the bottom surface of the deposited powder layer and standing on a position regulator 29. The camera 28 is preferably a CCD camera of the line sensor type and plane sensor type by which the foreign matter particles in the deposited resin powder layer can be detected through the transparent bottom of the agitation vessel 13. Along with the progress of CCD cameras in recent years, a CCD camera of high detecting power is now available on the market. When the transparent bottom of the agitation vessel 13 has a large surface area not to be covered by a single shot of the camera 28, it is possible that two or more cameras are installed below the agitation vessel 13 to share different fields of vision of the transparent bottom or that the whole surface area of the transparent bottom is covered by several shots of a single camera moved to varied positions relative to the transparent bottom. Since it is desirable that foreign matter particles of 100 to 150 $\mu$m dimensions can be detected by the camera 28, the pixels of the CCD camera should have dimensions of 100 $\mu$m by 100 $\mu$m or finer.

Figure 4:
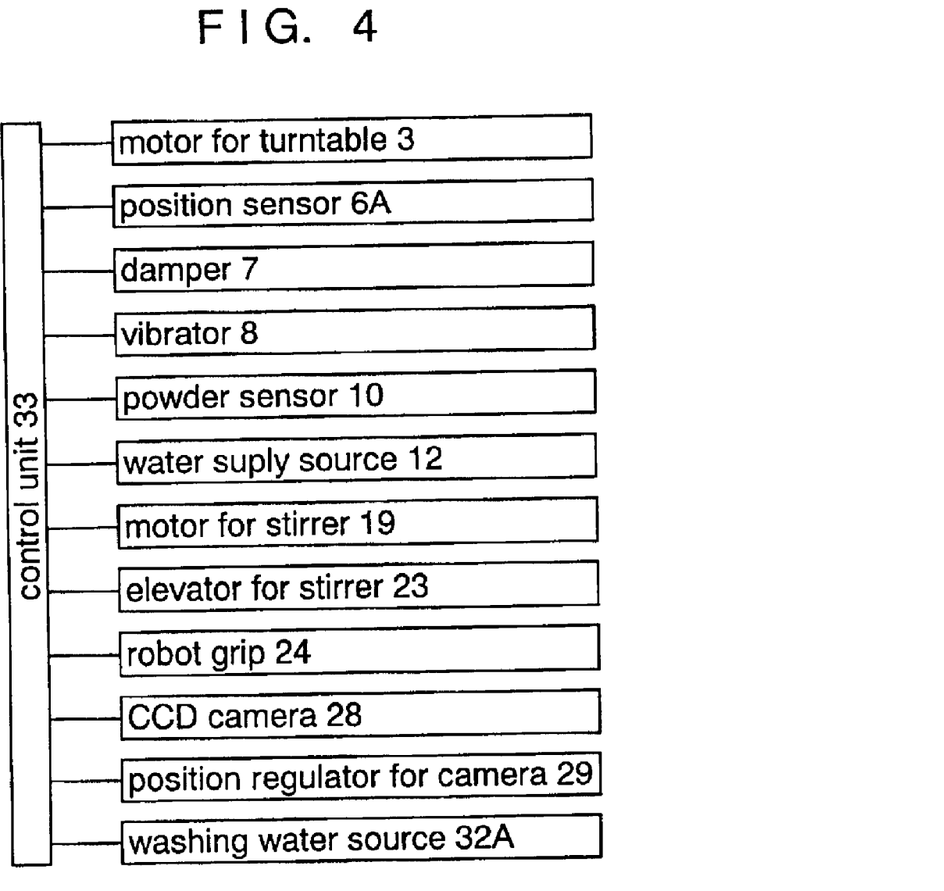
FIG. 4 is a block diagram of the system under control of the control circuit unit for bringing the inventive apparatus system into a sequential linkage motion.

It is preferable that the above described operations and movements of various parts of the inventive apparatus system for detecting and counting foreign matter particles in a VC resin powder are in a sequential linkage motion as controlled by an electronic control unit 33 which, as is shown by the block diagram of FIG. 4, controls the motor 3 for revolution of the turntable 5, position sensor 6A, damper 7, vibrator 8, feed powder sensor 10, water supply source 12 (not shown in the figure) for dispersion water, stirrer motor 19, elevator for stirrer means 18, robot grip 24 for vessel transfer, CCD camera 28, position regulator 29 for the CCD camera and washing water supply source 32A (not shown in the figure).

The various parts of the inventive apparatus system are sequentially controlled by the control unit 33 in the following steps described by making reference to FIGS. 1 to 4.

Step 1: The motor 3 of the automatic powder feed unit 2 is operated by the command from the control unit 33 so that the turn-table 5 is revolved in the direction indicated by the arrow 5H by an angle of, for example, 45° assuming that the turntable 5 carries eight hoppers 6,6 each containing a specified amount of the resin powder sample so that one of the hoppers 6,6 is brought to a correct position for feeding the powder sample to the agitation vessel 13 below. Revolution of the motor 3 is interrupted by the signal coming from the position sensor 6A which detects the position of the hopper 6.

Step 2: When the movements of the parts in Step 1 are all over, the damper 7 is set to open and the vibrator 8 is brought into operation by the command from the control unit 33 so that the powder sample P in the hopper 6 is introduced into the agitation vessel 13 through the feed conduit 9. The damper 7 is set to closure and the vibrator 8 is turned off by the signal coming from the powder feed sensor 10 which detects termination of powder feeding from the hopper 6. Concurrently or thereafter, the water supply source 12 is brought into operation by the command from the control unit 33 so that a specified volume of dispersion water, optionally, admixed with a surface active agent is poured into the agitation vessel 13 through the water supply tube 11.

Step 3: As the movements of the parts in Step 2 are all over, the elevator 23 of the stirrer means 18 is actuated by the command from the control unit 33 so that the stirrer blade 21 is brought to the lowered working position 21A in the dispersion water and the resin powder P in the agitation vessel 13. Thereafter, rotation of the stirrer blade 21 is started as commanded by the control unit 33 to disperse the resin particles in the dispersion water by continuing agitation for a specified length of time to prepare a uniform aqueous dispersion of the resin particles. Then, the elevator 23 is again actuated to pull up the stirrer means 18 to the pulled-up standby position and the aqueous dispersion is allowed to stand still in the vessel 13 for a specified length of time to effect settling of the resin particles together with foreign matter particles therein forming a deposited powder layer on the bottom of the vessel 13.

Step 4: As the movements in Step 3 are all over, the CCD camera 28 and the camera position regulator 29 are brought into operation by the command from the control unit 33 so that the whole area of the lower surface of the deposited powder layer is scanned by the camera 28 through the transparent bottom wall of the vessel 13. The image data obtained in the CCD camera 28 are sent to the control unit 33 and processed there to give the number of the foreign matter particles contained in the VC resin powder P.

Step 5: As the movements in Step 4 are all over, the command from the control unit 33 is directed to the robotized transfer unit for the agitation vessel 13, which is grasped by the robot grip 24 and taken up above the annular base 15. Thereafter, the transfer unit is moved along the horizontal guide rail 26 on the base table 1 and the vessel 13 is brought just above the drain funnel 31 where the vessel 13 is turned over upside-down to be evacuated of the aqueous dispersion therein. When the vessel 13 becomes emptied, washing water from the washing water supply source 32A (not shown in the figures) is ejected from the water nozzle 32 for a specified length of time so that the inside of the agitation vessel 13 is completely freed from any solid materials. Thereafter, the vessel 13 is raised up to a normal upright disposition and brought back onto the annular base 15 by means of the robotized vessel transfer unit followed by the withdrawal of the transfer unit to the standby position illustrated in FIG. 1.

When the movements in Step 5 are over, the control unit 33 is programmed to automatically repeat the sequence of Step 1 through Step 5 as many times as the number of the VC resin powder samples for inspection of foreign matter particles.

In the following, the method of the present invention for detecting and counting foreign matter particles in a VC resin powder and an automatic apparatus system for practicing the inventive method are described in more detail by way of Examples and Comparative Examples, which, however, never limit the scope of the invention in any way.

EXAMPLE 1

A flat-bottom cylindrical glass bottle of 1 gallon capacity having a narrowed mouth, of which the bottom had a diameter of 25 cm, was charged with 1 kg of a homopolymeric polyvinyl chloride resin powder of a commercial grade (TK 1000, a product by Shin-Etsu Chemical Co.) and 2 kg of deionized water and then an aqueous solution of 10 g of a polyethyleneoxide in 100 g of deionized water was added to the vessel. As tightly sealed with a covering, the glass bottle was vigorously shaken for 3 minutes by hand to effect dispersion of the resin particles into the aqueous medium. The glass bottle containing the aqueous dispersion of the resin particles formed as above was kept standing still for 5 minutes to cause settling of the resin particles onto the flat bottom forming a layer of the deposited resin particles having an average thickness of 3.8 cm. The lower surface of the thus deposited powder layer was examined through the transparent glass bottom of the bottle taking 3 minutes. The number of foreign matter particles determined by 30 times repetition of the same testing procedure ranged from 38 to 54 in each of the 18 testing runs after omission of the smallest 6 and largest 6 values among the 30 values.

EXAMPLE 2

The testing procedure was substantially the same as in Example 1 except that the amount of water initially taken was decreased from 2 kg to 1 kg. The layer of the VC resin particles deposited on the flat bottom of the vessel had an average thickness of 3.8 cm. The number of foreign matter particles detected by 30 times repetition of the procedure ranged from 32 to 52 in the 18 testing runs after omission of the smallest 6 and largest 6 values among the 30 values indicating good reproducibility of the results obtained by the method.

EXAMPLE 3

A glass-made Erlenmeyer flask of 3 liter capacity having a flat bottom of 15 cm diameter was charged with 10 g of a polyvinyl chloride resin of a commercial grade (TK 700, a product by Shin-Etsu Chemical Co.) and 1 kg of water of in-plant supply followed by the addition of an aqueous solution of 1 g of a sodium alkylbenzene sulfonate in 100 g of water. The flask as tightly stoppered was vigorously shaken by hand for 1 minute to effect dispersion of the resin particles in the aqueous medium and then the flask was kept standing still to allow settling of the resin particles onto the bottom of the flask to form a layer of the deposited resin particles having a thickness of 0.2 cm. The number of foreign matter particles deposited on the bottom of the flask was visually counted through the bottom of the flask taking about 3 minutes. This testing procedure was repeated 50 times to obtain results that the number of the foreign matter particles detected in each testing run was 2 or less in the 30 testing runs after omission of the smallest 10 and largest 10 values among the 50 values obtained.

EXAMPLE 4

The testing procedure was substantially the same as in Example 3 except that the amount of the VC resin powder introduced into the 3 liter flask was increased from 10 g to 100 g to form a layer of the deposited resin particles having an average thickness of 1.5 cm in each of the testing runs repeated 50 times. The number of foreign matter particles detected ranged from 7 to 10 in each of the 30 testing runs after omission of the smallest 10 and largest 10 values among the 50 values.

EXAMPLE 5

The testing procedure was just the same as in Example 4 described above except that the same testing procedure was repeated 100 times as a total. The number of foreign matter particles detected ranged from 8 to 10 in each of the 60 testing runs after omission of the smallest 20 and largest 20 values among the 100 values.

EXAMPLE 6

A cylindrical stainless steel vessel of 2 liter capacity having a 10 mm thick glass bottom of 15 cm diameter was charged with 200 g of a polyvinyl chloride resin-based compound, which was a composite prepared by compounding 100 parts by weight of a polyvinyl chloride resin (TK 1000, supra), 50 parts by weight of dioctyl phthalate as a plasticizer and 2 parts by weight of an organic tin compound (TS-101, a product by Akishima Chemical Co.) as a stabilizer, and 1 kg of water of in-plant supply followed by further addition of an aqueous solution of a sodium alkylbenzenesulfonate in 100 g of water to give a dispersion mixture which was agitated for 3 minutes with a stirrer blade inserted thereinto to give a uniform aqueous dispersion of the resin compound particles into the aqueous medium. The bottle was then kept standing still for 5 minutes to allow settling of the particles onto the glass bottom of the bottle to form a layer of the deposited particles having an average thickness of 2.2 cm. The number of foreign matter particles deposited on the bottom of the bottle was counted visually through the glass bottom taking 3 minutes. This testing procedure was repeated 30 times to give a result that the number of the foreign matter particles detected ranged from 11 to 19 in the 18 testing runs after omission of the smallest 6 and largest 6 values among the 30 values.

EXAMPLE 7

The testing procedure was substantially the same as in Example 6 except that the amount of the VC resin compound introduced into the bottle was increased from 200 g to 500 g in each of the 30 times-repeated testing runs. The layer of the particles deposited on the bottom of the vessel had an average thickness of 5.0 cm. The number of foreign matter particles detected ranged from 20 to 36 after omission of the smallest 6 and largest 6 values among the 30 values.

COMPARATIVE EXAMPLE 1

A 1 kg portion of a polyvinyl chloride resin powder of the same grade as tested in Example 1 was spread over a paper sheet in a layer from which foreign matter particles were manually picked out one by one with tweezers taking 30 minutes. This manual testing procedure was repeated 30 times. The number of the foreign matter particles thus picked out ranged from 46 to 62 in the 18 testing runs after omission of the smallest 6 and largest 6 values among the 30 values.

COMPARATIVE EXAMPLE 2

A 1 kg portion of a polyvinyl chloride resin powder of the same grade as tested in Example 1 was portion-wise mounted on a vibrator (Model Syntron Vibrator, made by Syntron Co.) and was moved thereon under vibration to run down in a streaky form, on which the number of foreign matter particles was visually counted taking 5 minutes. This counting procedure was repeated 30 times. The number of the foreign matter particles per kg of the resin powder ranged from 16 to 48 in the 18 testing runs after omission of the smallest 6 and largest 6 values among the 30 values.

Following is a general description of the counting procedure of foreign matter particles in a VC resin powder by using the inventive automatic counting apparatus system illustrated in FIG. 1.

Besides an actual lot sample of a commercial VC resin product (TK 1000, supra), referred to as the Sample I hereinafter, two simulation samples, referred to as the Samples II and III hereinafter, were prepared by uniformly blending a 1 kg portion of the same VC resin powder as above with 200 pieces or 400 pieces, respectively, of black-colored foreign matter particles of 0.3 mm dimension.

Counting of the foreign matter particles in the above prepared Samples I, II and III was conducted by operating the automatic counting apparatus system as illustrated in FIG. 1, in which: each of the eight hoppers 6,6 supported on a turntable 5 had a capacity of 300 ml; the agitation vessel 13 was a Pyrex glass-made, flat-bottom cylindrical vessel of about 1.2 liter capacity having an inner diameter of 100 mm and depth of 150 mm; the stirrer blade 21 was a paddle blade of 75 mm by 10 mm dimensions; the CCD camera 28 was a Model DXC-900 camera (a product by Sony Corp.); a ring-type illuminating lamp (not shown in the figure) was provided in the space between the agitation vessel 13 and the CCD camera 28; a 300 ml volume of deionized water was introduced into the agitation vessel 13 in each counting run by way of the water-supply tube 11; the agitating time for dispersion of the VC resin particles in water was 30 seconds; the settling time of the particles in the aqueous dispersion by standing still after completion of the agitation was 1 minute; the ejection time of washing water out of the water nozzle 32 was 30 seconds in each time; and the various parts of the apparatus system were sequentially operated by means of a control unit manufactured by NEC Corp.

EXAMPLE 8

By operating the above described automatic counting apparatus system under the above described conditions, eight consecutive runs of counting of foreign matter particles were conducted for the Sample I taking 4 minutes in each run by first introducing a 50 g portion of the sample powder into each of the eight hoppers 6,6. The layer of the resin particles deposited on the bottom of the vessel had an average thickness of 1.5 cm. The number of foreign matter particles in the eight counting runs ranged from 2 to 3 per 50 g sample.

EXAMPLE 9

The procedure for counting of foreign matter particles in a VC resin powder was substantially the same as in Example 8 except that the Sample I was replaced with the same amount of the Sample II. The time taken for each counting run was 4 minutes and the number of foreign matter particles detected in the eight counting runs ranged from 9 to 12 per 50 g of the sample powder.

EXAMPLE 10

The procedure for counting of foreign matter particles in a VC resin powder was substantially the same as in Example 8 except that the Sample I was replaced with the same amount of the Sample III. The time taken for each counting run was 4 minutes and the number of foreign matter particles detected in the eight counting runs ranged from 18 to 21 per 50 g of the sample powder.

COMPARATIVE EXAMPLE 3

In a similar manner to Comparative Example 1, numbers of foreign matter particles in Samples I, II and III were counted by manually picking out the particles using a spatula in a bright room from a layer of 50 g of the powder sample spread over a clean white paper sheet. Eight runs a total of counting were undertaken by four testing workers each for two runs with one of the three Samples taking about 28 minutes per run on an average. The numbers of the foreign matter particles as detected in eight 8 runs ranged from 2 to 3, from 10 to 13 and from 21 to 24 per 50 g of the Samples I, II and III, respectively.

COMPARATIVE EXAMPLE 4

In a similar manner to Comparative Example 2, visual counting of the foreign matter particles was conducted for a 50 g portion of each of the Samples I, II and III by use of a vibrator forming a streak of the resin powder running down at a rate of about 4 g/minute. Eight runs a total of counting were undertaken by four testing workers each for two runs with one of the three Samples taking about 13 minutes per run on an average. The numbers of the foreign matter particles as detected in eight runs ranged from 1 to 2, from 7 to 11 and from 13 to 20 per 50 g of the Samples I, II and III, respectively.

What is claimed is:

1. A method for detecting and counting foreign matter particles contained in a vinyl chloride-based polymeric resin powder which comprises the steps of:
    (a) forming or introducing an aqueous dispersion of the resin powder containing foreign matter particles in or into a vessel having a flat bottom made at least partly from a transparent material;
    (b) allowing the aqueous dispersion standing still in the vessel to effect settling of particles of the resin powder and the foreign matter particles forming a layer of deposited particles on the bottom of the vessel; and
    (c) counting the number of the foreign matter particles appearing in the layer of the deposited particles by viewing from below through the transparent bottom of the vessel.

2. The method for detecting and counting foreign matter particles contained in a vinyl chloride-based polymeric resin powder as claimed in claim 1 in which the aqueous dispersion of the resin powder is formed in step (a) by agitating the resin powder and water in the vessel.

3. The method for detecting and counting foreign matter particles contained in a vinyl chloride-based polymeric resin powder as claimed in claim 1 in which the amount of water in the aqueous dispersion of the resin powder is in the range from 1 to 10000 parts by weight per part by weight of the resin powder.

4. The method for detecting and counting foreign matter particles contained in a vinyl chloride-based polymeric resin powder as claimed in claim 1 in which the aqueous dispersion of the resin powder contains a dispersion aid for particles of the resin powder.

5. The method for detecting and counting foreign matter particles contained in a vinyl chloride-based polymeric resin powder as claimed in claim 4 in which the dispersion aid is a surface active agent.

6. The method for detecting and counting foreign matter particles contained in a vinyl chloride-based polymeric resin powder as claimed in claim 5 in which the amount of the surface active agent is in the range from 0.0000001 to 0.1 part by weight per part by weight of the water in the aqueous dispersion.

7. The method for detecting and counting foreign matter particles contained in a vinyl chloride-based polymeric resin powder as claimed in claim 1 in which the length of time in step (b) for settling of the particles is at least 10 seconds.

8. The method for detecting and counting foreign matter particles contained in a vinyl chloride-based polymeric resin powder as claimed in claim 1 in which counting of the number of foreign matter particles in step (c) is conducted on a photographic image of the lower surface of the deposited particle layer recorded by viewing through the transparent bottom of the vessel.

9. The method for detecting and counting foreign matter particles contained in a vinyl chloride-based polymeric resin powder as claimed in claim 8 in which counting of the number of foreign matter particles in step (c) is conducted by electronic processing of the image data of the lower surface of the deposited particle layer recorded in a CCD camera by viewing through the transparent bottom of the vessel.

10. The method for detecting and counting foreign matter particles contained in a vinyl chloride-based polymeric resin powder as claimed in claim 1 in which the layer of the deposited particles formed in step (b) has a thickness in the range from 0.1 to 6.0 cm.

11. An apparatus system for automatically detecting and counting foreign matter particles contained in a vinyl chloride-based polymeric resin powder which comprises, as an assembly:
    (A) a vessel having a flat bottom made at least partly from a transparent material;
    (B) a feeder means capable of introducing a specified amount of the resin powder into the vessel (A):
    (C) a water supply means capable of introducing a specified volume of water into the vessel (A):
    (D) a stirrer means capable of agitating the resin powder and the water in the vessel (A) to form an aqueous dispersion of the resin particles in the water; and
    (E) a photographic means capable of recording an image of the transparent bottom of the vessel (A).

12. The apparatus system as claimed in claim 11 which further comprises:
    (F) a control unit capable of controlling the elements (A) to (E) into a sequential linkage motion.

13. The apparatus system as claimed in claim 10 in which the photographic means is a CCD camera.

14. The apparatus system as claimed in claim 13 in which the pixels of the CCD camera have dimensions of 100 $\mu$m by 100 $\mu$m or finer.

15. The apparatus system as claimed in claim 13 in which the control unit (F) further has a data analyzer for the image data recorded in the CCD camera.

* * * * *